(12) United States Patent
Flohr et al.

(10) Patent No.: US 8,712,007 B2
(45) Date of Patent: Apr. 29, 2014

(54) METHOD AND COMPUTED TOMOGRAPHY DEVICE AND DATA STORAGE MEDIUM FOR PERFORMING A DYNAMIC CT EXAMINATION ON A PATIENT

(75) Inventors: Thomas Flohr, Uehlfeld (DE); Bernhard Schmidt, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 36 days.

(21) Appl. No.: 13/451,134

(22) Filed: Apr. 19, 2012

(65) Prior Publication Data

US 2012/0269318 A1    Oct. 25, 2012

(30) Foreign Application Priority Data

Apr. 20, 2011    (DE) .......................... 10 2011 007 741

(51) Int. Cl.
*A61B 6/00*    (2006.01)

(52) U.S. Cl.
USPC .................................. 378/16; 378/4; 378/11

(58) Field of Classification Search
USPC ...................... 378/4, 11, 15, 16, 20, 205, 901
See application file for complete search history.

(56) References Cited

U.S. PATENT DOCUMENTS

| | | | |
|---|---|---|---|
| 6,320,929 B1 | 11/2001 | Von Der Haar | |
| 7,277,522 B2 * | 10/2007 | Bruder et al. | 378/14 |
| 7,403,597 B2 | 7/2008 | Raupach | |
| 8,094,775 B2 * | 1/2012 | Noshi et al. | 378/15 |

* cited by examiner

*Primary Examiner* — Jurie Yun
(74) *Attorney, Agent, or Firm* — Schiff Hardin LLP

(57) ABSTRACT

In a computed tomography apparatus and operating method, a radiation source and radiation detector are rotated around a system axis, and a patient support plate and diaphragm elements of a diaphragm associated with the x-ray source are also movable in the direction of the system axis. Movement of the patient support plate and the diaphragm plates between respective end positions is coordinated during a dynamic computed tomography examination of a subject so as to reduce and homogenize the dose of x-ray radiation to which the subject is exposed during the examination.

15 Claims, 4 Drawing Sheets

METHOD AND COMPUTED TOMOGRAPHY DEVICE AND DATA STORAGE MEDIUM FOR PERFORMING A DYNAMIC CT EXAMINATION ON A PATIENT

BACKGROUND OF THE INVENTION

1. Field of the Invention

The invention relates to a method for operating a CT (computed tomography) device and a computed tomography device for performing a dynamic CT examination on a patient, the computed tomography device being of the type having a gantry with a stationary part and a part that can be rotated around a system axis, with an x-ray radiation source and an x-ray radiation detector disposed opposite one another on the rotatable part, and a patient support plate that can be moved in the direction of the system axis. The invention also relates to a non-transitory data storage medium, on which program code is encoded that implements such a method.

2. Description of the Prior Art

In addition to conventional CT examinations, in which slice images or 3D images of a body region of a patient are reconstructed to obtain information about the morphology of the patient, so-called dynamic CT examinations are now established procedures, that are used to obtain functional information, for example about patient tissue. Contrast agents are frequently used in this type of computed tomography.

An example of such dynamic examination is a multiphase examination of the liver of a patient, of which images are produced in different time phases or different states, in order to be able to distinguish between different types of lesions in the liver for diagnostic purposes. In the case of the liver the different phases or states are produced by administering contrast agent, which is absorbed by the different types of lesions at different times. The multiphase examination of the liver therefore includes a so-called native phase, in which no contrast agent is present in the liver, a second arterial phase after the administration of contrast agent and a third venous phase after the administration of contrast agent, following the arterial phase. In order to be able to reconstruct images in all the liver phases, it is necessary to record x-ray projections of the body region containing the liver in all the liver phases over quite a long time period of approx. 30 to 50 seconds, for example to evaluate perfusion parameters.

According to a first method the body region of the patient containing the liver is positioned with the patient support plate in the measurement volume of the computed tomography device defined by the x-ray radiation source and the x-ray radiation detector and, with the patient support plate stationary, successive x-ray projections are recorded of the body region of the patient containing the liver, for image reconstruction purposes. A disadvantage of this recording technique is that the examinable body region is limited to the width of the x-ray radiation detector when viewed in the direction of the system axis or the longitudinal axis of the patient, and this cannot easily be extended, at least with existing computed tomography devices. Arbitrary patient movement and respiratory movement make it desirable to have greater coverage in the longitudinal direction of the patient when recording x-ray projections. FIG. 1 shows the described situation, with the width of the x-ray radiation detector or the extension A1 of an x-ray projection PR in the direction of the system axis SY defining the scan region S1 in the direction of the system axis SY or the body region of the patient P to be examined. The dose profile D1 of the dose of x-ray radiation applied to the patient P during the recording of x-ray projections is relatively homogeneous and is also based on the width of the x-ray radiation detector or the extension A1 of the x-ray projections PR in the direction of the system axis SY.

To avoid the disadvantages of the first method, a second method was created, in which while the measurement system remains otherwise the same, but during the recording of x-ray projections the patient support plate bearing the patient is moved forward and back periodically and continuously when viewed in the direction of the system axis or the longitudinal axis of the patient within a scan region S2, so that x-ray projections PR of a longer body region of the patient can effectively be recorded. Compared with the first method, the dose profile D2 of the dose of x-ray radiation applied to the patient during the recording of x-ray projections PR widens. The distribution of the dose when viewed in the direction of the longitudinal axis of the patient is however comparatively homogeneous. FIG. 2 shows the method, with which a larger or longer body region of the patient can be examined by moving the patient support plate holding said patient, while the x-ray radiation detector remains in a fixed position.

Computed tomography devices are now being used that have a wider x-ray radiation detector when viewed in the direction of the system axis than previously used computed tomography devices. While some years ago so-called 16-slice detectors were still the standard for x-ray radiation detectors, the standard is now 64-slice detectors, or x-ray radiation detectors with even more slices. In the case of wider x-ray radiation detectors, assuming that the scan region does not get longer, since the anatomy of the patient does not change, the shape of the dose profile of the dose of x-ray radiation applied to the patient during the recording of x-ray projections changes. Particularly in the case of a relatively short scan region compared with detector coverage, there is a clear rise in the dose of x-ray radiation in the central body section of the body region of the patient to be examined, which is exposed almost continuously to x-ray radiation despite the movement of the patient support plate, without the additionally obtained information being necessary for diagnostic purposes. FIG. 3 illustrates the problem. While scan region S3 corresponds to scan region S2 from FIG. 2, the width of the x-ray radiation detector or the extension A3 of an x-ray projection PR in the direction of the system axis is much larger than the width of the x-ray radiation detector or the extension A1 of an x-ray projection PR in the direction of the system axis from FIG. 2. Despite the movement of the patient support plate, the body section of the patient to be assigned to the center of the scan region is permanently exposed, so the dose profile D3 results with a clear rise in the dose of x-ray radiation in the central region.

SUMMARY OF THE INVENTION

An object of the invention is to provide a method and a computed tomography device for performing a dynamic CT examination on a patient and a data storage medium of the type described initially, wherein the dose of x-ray radiation applied to a patient during a dynamic CT examination is reduced and homogenized over the examined body region.

According to the invention this object is achieved by a method for operating a computed tomography device for performing a dynamic CT examination on a patient, having a gantry with a stationary part and a part that can be rotated about a system axis, on which rotatable part an x-ray radiation source and an x-ray radiation detector are disposed opposite one another, a diaphragm assigned to the x-ray radiation source, which has diaphragm elements that can be moved in the direction of the system axis to limit an x-ray radiation beam originating from the x-ray radiation source in the direction of the system axis and a patient support plate that can be moved in the direction of the system axis. In accordance with the invention, for a dynamic CT examination of a body region of the patient, the patient support plate is preferably moved forward and back in the direction of the system axis between a first end position and a second end position of the patient support plate, and at the same time the diaphragm elements of the diaphragm are preferably moved forward and back in the direction of the system axis between a first end position and a second end position of the diaphragm elements.

In accordance with the invention, the preferably periodic movement of the patient support plate in the direction of the system axis is overlaid with a preferably periodic movement of the diaphragm elements, e.g. diaphragm blades, of a diaphragm assigned to the x-ray radiation source in the direction of the system axis during the recording of x-ray projections, in order to be able to control which body section of the body region to be examined or of the scan region is to be exposed to x-ray radiation. Specific control, in particular of the movement of the diaphragm elements, not only allows the dose of x-ray radiation applied to the patient during the dynamic CT examination to be influenced and preferably reduced, but also allows the dose distribution or dose curve to be influenced, in particular homogenized.

The method is primarily provided for dynamic CT examinations, in which the scan region or the body region of a patient to be examined is relatively small given the width of the x-ray radiation detector of the computed tomography device or the extension of an x-ray projection completely covering the x-ray radiation detector when viewed in the direction of the system axis. This is generally the case when the scan region is, for example, shorter or smaller than double the width of the x-ray radiation detector when viewed in the direction of the system axis of the computed tomography device.

According to one embodiment of the invention the patient support plate and the diaphragm elements are moved simultaneously in the two opposing directions of the system axis, preferably periodically forward and back relative to one another. Both the diaphragm elements and the patient support plate are moved linearly at preferably constant movement speed in each instance, apart from the reversal points or reversal positions, in the two directions of the system axis. This also allows a higher scan speed to be achieved than with just the movement of the patient support plate.

According to another embodiment of the invention the diaphragm elements, viewed in the direction of the system axis, have a certain opening width to limit the x-ray radiation beam originating from the x-ray radiation source in the direction of the system axis, this opening width being selected so that the x-ray radiation beam, when it strikes the x-ray radiation detector, when viewed in the direction of the system axis, covers only part of the detector surface of the x-ray radiation detector. The x-ray radiation beam is therefore shaped or limited specifically in the direction of the system axis, so that only part of the x-ray radiation detector is covered and therefore only part of the body section of the body region to be examined that can be exposed per se with each x-ray projection. Specific control of the movement of the diaphragm elements thus allows over-scanning to be avoided in the central body section of the body of the patient to be examined.

According to a further variant of the invention, the patient support plate and the diaphragm elements are moved relative to one another in opposing directions so that, while the patient support plate is being moved from its first end position into its second end position and at the same time the diaphragm elements are being moved from their first end position into their second end position, the x-ray radiation beam covers the x-ray radiation detector completely when viewed in the direction of the system axis. To this end, the movement speeds for the patient support plate and the diaphragm elements are to be selected inter alia as a function of the size of the scan region, the opening width of the diaphragm elements and the width of the x-ray radiation detector when viewed in the direction of the system axis.

As mentioned above, the diaphragm elements have a certain opening width, when viewed in the direction of the system axis, to limit the x-ray radiation beam originating from the x-ray radiation source in the direction of the system axis, this opening width remaining constant according to one embodiment of the invention during the movement of the diaphragm elements in the direction of the system axis.

According to a further embodiment of the invention, the focus of the x-ray radiation source during the movement of the diaphragm elements in the direction of the system axis is moved in the same direction as the diaphragm elements in respect of the system axis. Depending on the position of the diaphragm elements or the opening width of the diaphragm elements relative to the x-ray radiation source, the focus is therefore tracked on the anode of the x-ray radiation source in the direction of the system axis.

The focus is preferably moved spasmodically, in other words following the principle of the so-called springing focus.

According to a further embodiment of the invention, as the patient support plate and the diaphragm elements are being moved, x-ray projections of the body region of the patient are preferably recorded from different directions and images of the body region of the patient are reconstructed.

The object of the invention is also achieved by a computed tomography device for performing a dynamic CT examination on a patient, having a gantry with a stationary part and a part that can be rotated about a system axis, on which rotatable part an x-ray radiation source and an x-ray radiation detector are disposed opposite one another, a diaphragm being assigned to said x-ray radiation source, which has diaphragm elements that can be moved in the direction of the system axis to limit an x-ray radiation beam originating from the x-ray radiation source in the direction of the system axis, a patient support plate that can be moved in the direction of the system axis and a computing facility, and that has a control unit configured to implement one or all embodiments of the method described above.

The above object also is achieved in accordance with the present invention by a non-transitory, computer-readable data storage medium encoded with programming instructions (program code) that, when the storage medium is loaded into a computerized control unit of a computed tomography apparatus, cause the control unit to operate the computed tomography apparatus to implement any or all of the embodiments of the method described above.

DESCRIPTION OF THE PREFERRED EMBODIMENTS

Figure 1:
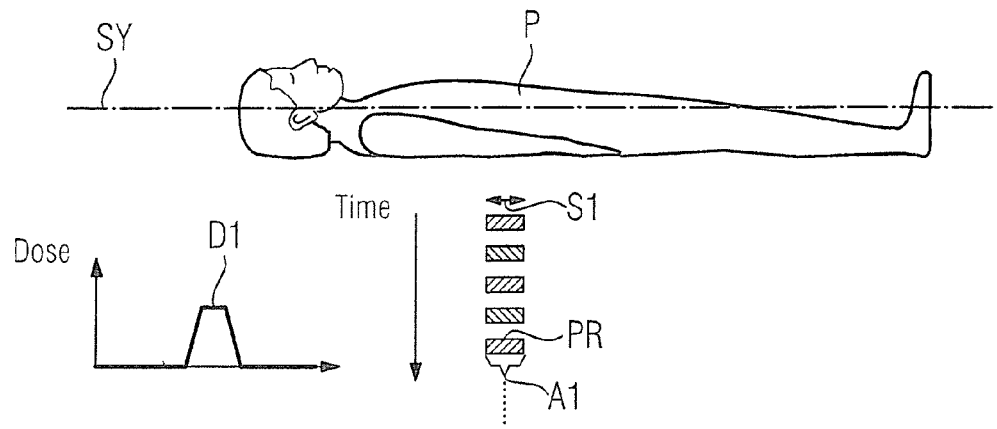
FIG. 1 to FIG. 3 show principles of dynamic CT examinations of a patient according to the prior art.
Figure 2:
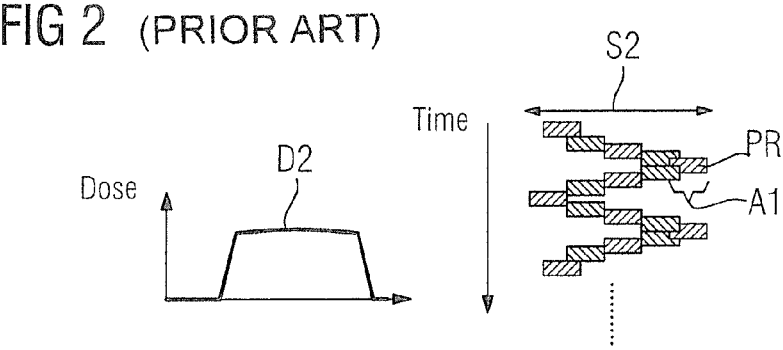

Identical element or elements of identical function are shown with the same reference characters in all the figures. The diagrams in the figures are schematic and not necessarily to scale. Without restricting its generality, the computed tomography device 11 is only examined below to the extent that this is deemed necessary for an understanding of the invention.

Figure 4:
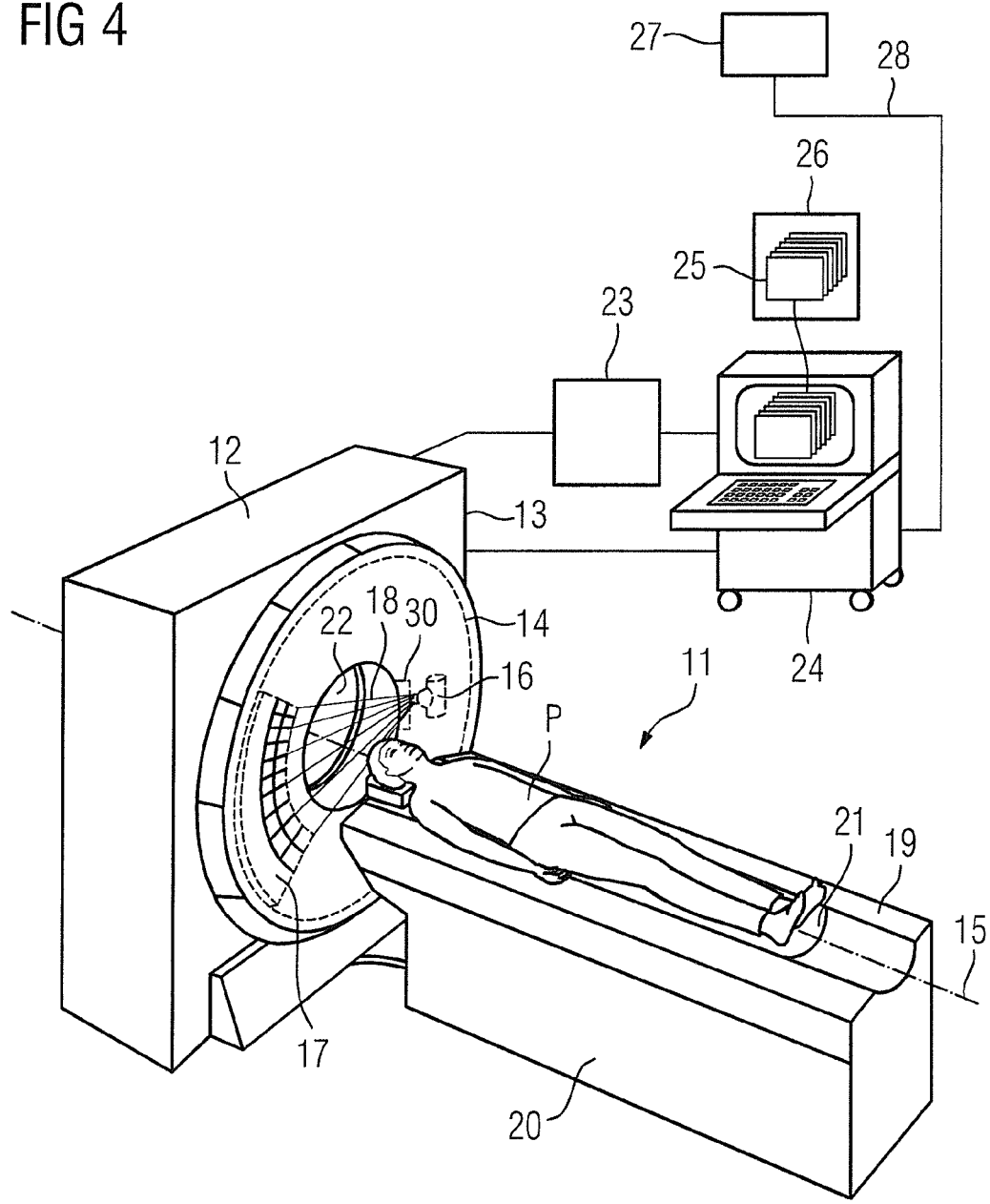
FIG. 4 shows a computed tomography device according to the invention.

The computed tomography device 11 shown in FIG. 4 has a gantry 12 with a stationary part 13 and a part 14 that can be rotated about a system axis 15. In the present exemplary embodiment of the invention the rotatable part 14 has an x-ray system, which comprises an x-ray radiation source 16 and an x-ray radiation detector 17, which are disposed opposite one another on the rotatable part 14. During operation of the computed tomography device 11 x-ray radiation 18 is emitted from the x-ray radiation source 16 in the direction of the x-ray radiation detector 17, penetrates a measurement object and is detected by the x-ray radiation detector 17 in the form of measurement data or measurement signals.

The computed tomography device 11 also has a patient couch 19 to support a patient P to be examined. The patient couch 19 comprises a couch base 20, on which a patient support plate 21 provided to actually support the patient P is disposed. The patient support plate 21 can be moved relative to the couch base 20 in the direction of the system axis 15 in such a manner that it can be introduced, together with the patient P, into the opening 22 of the gantry 12 for the recording of 2D x-ray projections of the patient P, e.g. during a spiral scan.

The computational processing of the 2D x-ray projections recorded using the x-ray system and the reconstruction of slice images, 3D images or a 3D data record based on the measurement data or measurement signals of the 2D x-ray projections take place using a schematically illustrated image computer 23 of the computed tomography device 11.

The computed tomography device 11 also has a computing unit 24, which can be and is used to execute computing programs to operate and control the computed tomography device 11. The computing unit 24 does not have to be configured as a separate computing unit 24 here but can also be integrated in the computed tomography device 11.

In the present exemplary embodiment of the invention a computing program 25 is loaded into the computing unit 24, which implements the inventive method for performing a dynamic CT examination on a patient P. The computing program 25 here represents a specific operating mode for the computed tomography device 11 and can be loaded into the computing unit 24 from a portable data medium, for example from a CD 26 or memory stick, or even from a server 27 via a network 28, which may be a public or internal clinic or hospital network.

For a dynamic CT examination of the patient P according to the invention, for example for a dynamic CT examination of the body region of the patient P containing the liver using contrast agent, in the present exemplary embodiment of the invention a diaphragm 30 is assigned to the x-ray radiation source 16, the diaphragm 30 having two diaphragm elements or diaphragm blades 31 and 32, which can be moved in the two directions of the system axis 15. The movement of the diaphragm blades 31, 32 can be brought about by one or more electric drives (not shown), which are activated at least indirectly by the computing unit 25.

During the dynamic CT examination of the body region of the patient P containing the liver, a scan region S is first defined in the direction of the system axis 15, in which x-ray projections of the body region of the patient P are recorded from different directions over approx. 50 seconds. The scan region S, when viewed in the direction of the system axis 15, is larger than the width B of the x-ray radiation detector 17. In order to be able to record x-ray projections from the entire scan region S periodically, the patient support plate 21 must be moved forward and back periodically between a first end position $E_{1PL}$ and a second end position $E_{2PL}$. If in this process the x-ray radiation detector 17 were covered continuously over its entire width B when viewed in the direction of the system axis 15 by the x-ray radiation beam 18 originating from the x-ray radiation source 16, a relatively high dose of x-ray radiation would be applied to the patient P in the central body section of the body region to be scanned or examined, since a sort of over-scanning would take place there, without being able to use the additional information usefully.

For this reason the diaphragm elements 31, 32 of the diaphragm 30 are moved by a program controller counter to the patient support plate 21 in the direction of the system axis 15 from a first end position $E_{1diaphragm}$ into a second end position $E_{2diaphragm}$. The diaphragm blades 31, 32 here have a selectable opening width W when viewed in the direction of the system axis 15, so that, when it strikes the x-ray radiation detector 17, when viewed in the direction of the system axis 15, the x-ray radiation beam 18 originating from the x-ray radiation source 16 only covers part of the detector surface of the x-ray radiation detector 17. As the diaphragm blades 31, 32 are being moved and x-ray projections are being recorded, the opening width W remains constant.

The patient support plate 21 and the diaphragm blades 31, 32 are moved by a program controller in opposite directions relative to one another so that, as the patient support plate 21 is being moved from its first end position $E_{1PL}$ into its second end position $E_{2PL}$ and at the same time the diaphragm blades 31, 32 are being moved from their first end position $E_{1diaphragm}$ into their second end position $E_{2diaphragm}$, the x-ray radiation beam 18 covers the x-ray radiation detector 17 completely when viewed in the direction of the system axis 15. To this end the movement speeds for the patient support plate 21 and the diaphragm blades 31, 32 should be selected or set correspondingly inter alia as a function of the size of the scan region S, the opening width W of the diaphragm blades 31, 32 and the width B of the x-ray radiation detector 17 when viewed in the direction of the system axis 15. These settings are assisted by the computing program 25, which preferably also has a graphical user interface, which can be displayed on the display apparatus of the computing unit 24.

In the present exemplary embodiment of the invention the x-ray radiation source 16 is an x-ray tube 16 with a springing focus. In the present exemplary embodiment of the invention the x-ray tube 16 has two foci F1 and F2 offset in the direction of the system axis 15. This makes it possible, as the diaphragm blades 31, 32 are being moved in the direction of the system axis 15, to move the respectively active focus, used to generate x-ray radiation, likewise in the direction of the system axis 15, in order to be able to generate an appropriate x-ray radiation beam 18 for the scan.

The sequence of the dynamic CT examination is illustrated in FIGS. 5 to 8 for four time points of a periodic movement.

Figure 5:
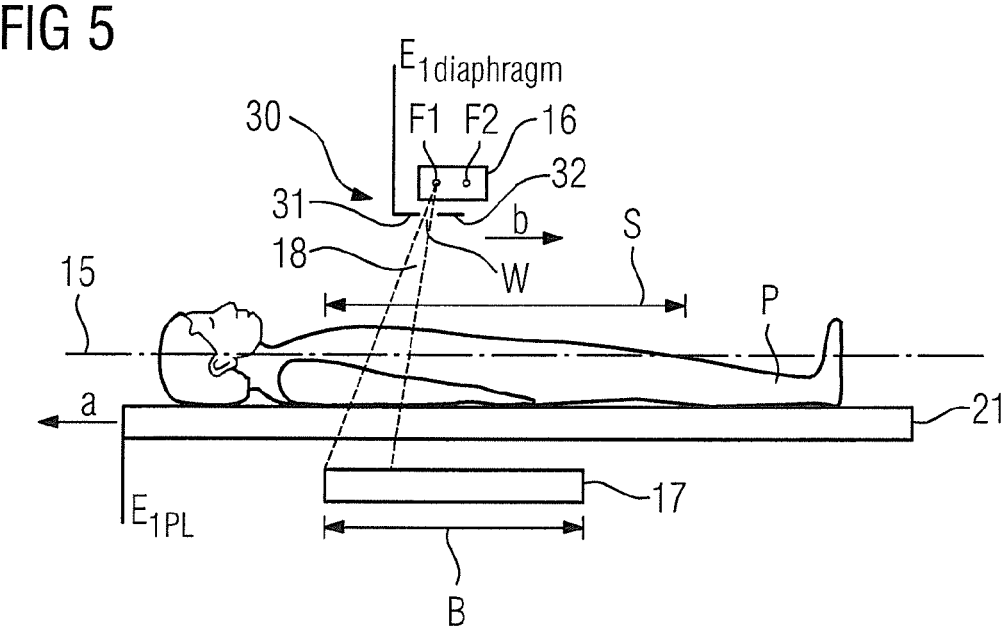
FIG. 5 to FIG. 8 show the principle of the dynamic CT examination of a patient according to the invention.

FIG. 5 shows the initial situation, in which the patient support plate 21 is in its first end position $E_{1PL}$ and the diaphragm blades 31, 32 are in their first end position $E_{1 diaphragm}$. In the present exemplary embodiment of the invention the opening width W of the diaphragm blades 31, 32 is selected so that approximately a quarter of the detector surface of the x-ray radiation detector 17 is covered by the x-ray radiation beam 18 originating from the focus F1 of the x-ray tube 16. Therefore with this configuration only part of the body region of the patient P to be scanned is penetrated by the x-ray radiation beam 18. The patient support plate 21 is now moved first in the direction of the arrow a and the diaphragm blades 31, 32 are moved in the opposite direction at the same time in the direction of the arrow b.

Figure 6:
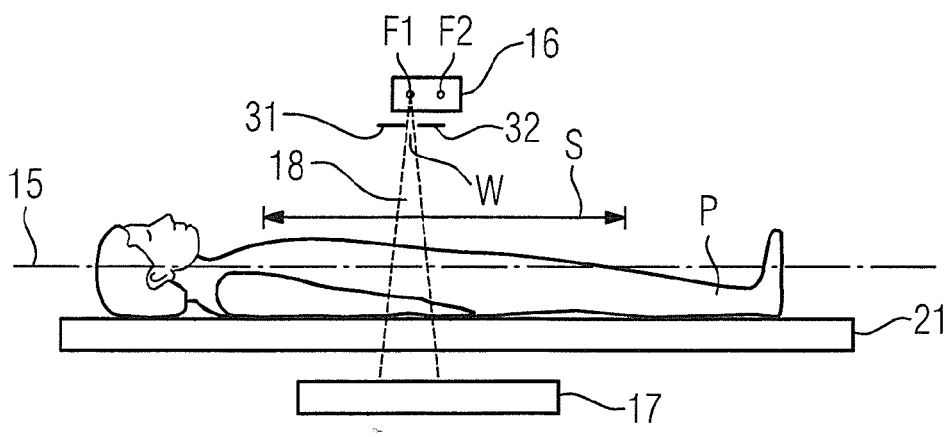

FIG. 6 shows the arrangement from FIG. 5 at a time point, when the patient support plate 17 has been moved a little in the direction of the arrow a and the diaphragm blades have been moved a little in the direction of the arrow b.

Figure 7:
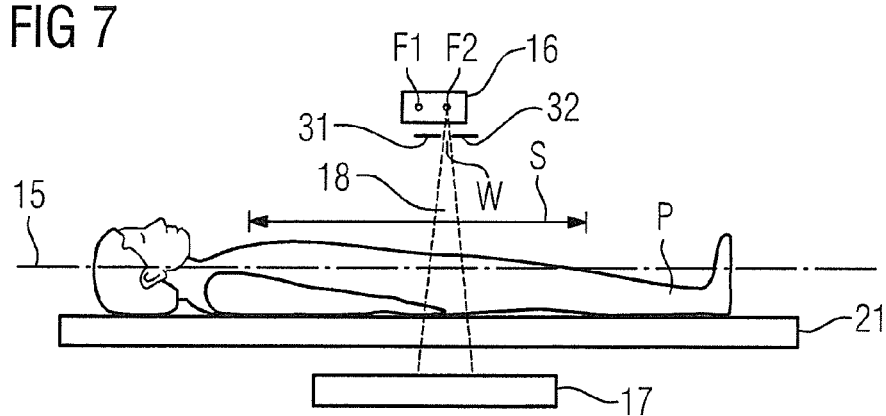

FIG. 7 shows the arrangement from FIG. 5 at a time point when the change from focus F1 to focus F2 has taken place, so that the focus follows the movement of the diaphragm blades 31, 32.

Figure 8:
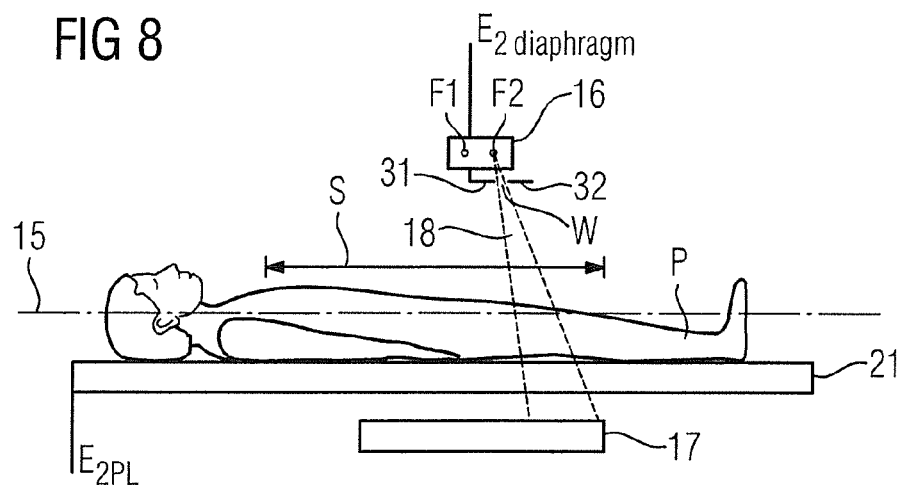

FIG. 8 shows the arrangement from FIG. 5 at a time point when the patient support plate 17 has reached its end position $E_{2PL}$ and the diaphragm blades 31, 32 have reached their end position $E_{2 diaphragm}$. The end position $E_{2PL}$ is also the reversal point for the movement of the patient support plate 17, which now moves in the direction of the arrow b. The end position $E_{2 diaphragm}$ is correspondingly the reversal point for the movement of the diaphragm blades 31, 32, which now move in the direction of the arrow a, therefore once again counter to the patient support plate 21. To this extent the sequence is now reversed (see also FIG. 8 to FIG. 5). The end positions $E_{1PI}$ and $E_{1 diaphragm}$ also represent reversal points for the movements.

While the patient support plate 21 and the diaphragm blades are moved forward and back periodically between their end positions, x-ray projections of the body region of the patient P to be examined are recorded continuously with the rotatable part 14 rotating about the patient P, from which projections slice images are preferably reconstructed with the aid of the image computer 23. Since the slice images generally follow one another in time, the liver can be displayed in different phases produced by the contrast agent, as described above.

Figure 3:
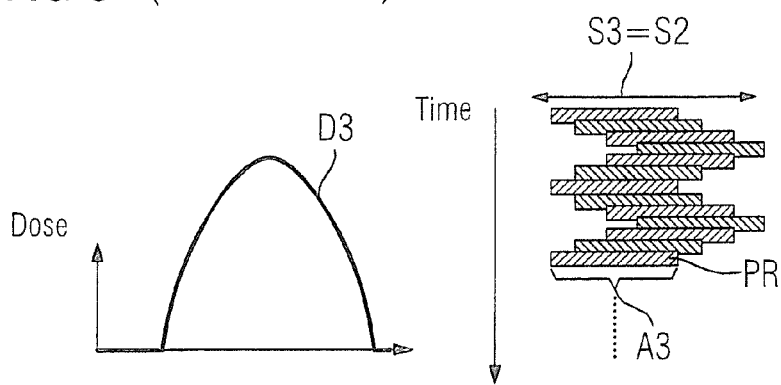
Figure 9:
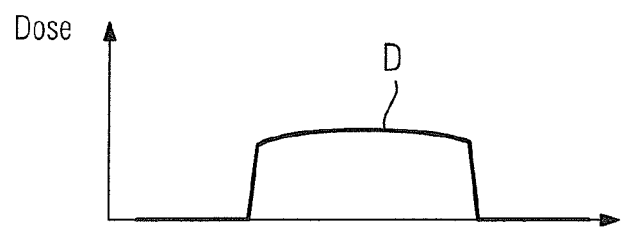
FIG. 9 shows the dose profile resulting during the dynamic CT examination.

It can be seen from FIGS. 5 to 8 that as a result of the inventive method no over-scanning takes place in the central body region of the body region of the patient P to be examined or scanned, so that a smaller dose of x-ray radiation is applied to the patient P than with a scan, in which only the patient support plate is moved periodically between its end positions with the x-ray radiation detector being covered completely with each x-ray projection (see also FIG. 3). The dose profile D shown in FIG. 9 is also more homogeneous.

The simultaneous movement of patient support plate 21 and diaphragm blades 31, 32 also means that a higher scan speed is achieved than with the movement of the patient support plate 21 alone. Also, to achieve the same scan speed as with the method in which only the patient support plate is moved, the speed of the patient support plate can be reduced as a result of the opposing movement of the diaphragm blades, so that the patient is also exposed to slower acceleration speeds to reach the respective speed.

Since the movement and positioning of the diaphragm blades can take place very quickly, dynamically triggered heart recordings are also possibly with the inventive method. For these the patient is moved forward and back with the patient support plate between two end positions according to his/her heart rate. If variations occur in the patient's heart rate, which, due to the inertia of the patient support plate, cannot be compensated for by a corresponding change in the movement speed of the patient support plate, the movement speed of the diaphragm blades is matched to the changed heart rate instead, in order to achieve the desired triggering during the recording of x-ray projections. It is clear from this that the movement speeds of the patient support plate and the diaphragm blades do not have to be constant but can vary or be matched to the recording situation.

In contrast to the described exemplary embodiment of the invention the focus of the x-ray radiation source does not necessarily have to be a spring focus. The x-ray radiation source can therefore also have just one stationary focus.

The described embodiment of the invention should generally only be considered to be exemplary. In particular settings such as the opening width of the diaphragm blades, the scan region, etc. can also be selected differently.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating a computed tomography apparatus comprising a gantry having a stationary part and a rotatable part mounted at the stationary part to rotate around a system axis, an x-ray radiation source and an x-ray radiation detector mounted on the rotatable part opposite each other, said x-ray source emitting an x-ray beam that propagates in a direction toward said system axis, a diaphragm associated with said x-ray source and comprising diaphragm elements that are movable relative to each other to limit a size of said x-ray beam and that are collectively movable in a direction of said system axis, and a patient support plate movable in the direction of said system axis, said method comprising:

implementing a dynamic computed tomography examination of a body region of a patient on said patient support plate by moving said patient support plate back and forth in said direction of said system axis between a first support plate end position and a second support plate end position;

while moving said patient support plate back and forth between said first and second support plate end positions, collectively moving said diaphragm elements of said diaphragm also back and forth in said direction of said system axis between a first diaphragm element end position and a second diaphragm element end position; and coordinating the back and forth movement of said support plate between said first and second support plate end positions and the back and forth movement of said diaphragm elements between said first and second diaphragm element end positions to homogenize a dose of x-ray radiation applied to the patient by said x-ray beam during said dynamic computed tomography examination.

2. A method as claimed in claim 1 comprising, when moving said patient support plate back and forth between said first and second support plate end positions and collectively moving said diaphragm elements back and forth between said first and second diaphragm element end positions, always moving said diaphragm elements and said patient support plate with respect to each other in opposite directions in the direction of said system axis.

3. A method as claimed in claim 2 comprising moving said patient support plate and collectively moving said diaphragm elements in said opposite directions to cause said x-ray beam, while the patient support plate is moving from said first support plate end position to said second support plate end position and while said diaphragm elements are collectively moving from said first diaphragm element end position to said second diaphragm element end position, to completely cover a detector surface of said x-ray radiation detector, viewed in the direction of the system axis.

4. A method as claimed in claim 1 comprising configuring said diaphragm elements, when viewed in the direction of the system axis, to have an opening width that limits said x-ray beam to cause said x-ray beam, when said x-ray beam strikes said x-ray radiation detector to cover, when viewed in the direction of the system axis, only a portion of a detector surface of the x-ray radiation detector.

5. A method as claimed in claim 1 comprising, when collectively moving said diaphragm elements between said first diaphragm element end position and said second diaphragm element end position, positioning said diaphragm elements with respect to each other to maintain a constant opening width that limits said x-ray beam, when viewed in said direction of said system axis.

6. A method as claimed in claim 1 wherein said x-ray radiation source has a focus from which said x-ray beam originates, and comprising moving said focus, during the collective movement of said diaphragm elements back and forth between said first diaphragm element end position and said second diaphragm element end position, in a same direction as said diaphragm elements with respect to said system axis.

7. A method as claimed in claim 6 comprising operating said focus as a springing focus.

8. A method as claimed in claim 1 comprising, while moving said support plate back and forth between said first and second support plate end positions and while collectively moving said diaphragm elements back and forth between said first and second diaphragm element end positions, operating said x-ray radiation source and said x-ray radiation detector to acquire a plurality of x-ray projections of said body region of the patient, and reconstructing an image of said body region of the patient from said plurality of x-ray projections.

9. A method as claimed in claim 1 comprising coordinating said back and forth movement of said support plate between said first and second support plate end positions and the back and forth movement of said diaphragm elements between said first and second diaphragm element end positions to give said dose of x-ray radiation a substantially rectangular dose profile.

10. A computed tomography apparatus comprising:
a gantry having a stationary part and a rotatable part mounted at the stationary part to rotate around a system axis, an x-ray radiation source and an x-ray radiation detector mounted on the rotatable part opposite each other;
said x-ray source being configured to emit an x-ray beam that propagates in a direction toward said system axis;
a diaphragm associated with said x-ray source and comprising diaphragm elements that are movable relative to each other to limit a size of said x-ray beam and that are collectively movable in a direction of system axis;
a patient support plate movable in the direction of said system axis;
a control unit configured to operate said x-ray radiation source and said diaphragm and said patient support plate to implement a dynamic computed tomography examination of a body region of a patient on said patient support plate by moving said patient support plate back and forth in said direction of said system axis between a first support plate end position and a second support plate end position;
said control unit being configured, while moving said patient support plate back and forth between said first and second support plate end positions, to collectively move said diaphragm elements of said diaphragm also in said direction of said system axis back and forth between a first diaphragm element end position and a second diaphragm element end position; and
said control unit being configured to coordinate back and forth movement of said support plate between said first and second support plate end positions and back and forth movement of said diaphragm elements between said first and second diaphragm element end positions to homogenize a dose of x-ray radiation applied to the patient by said x-ray beam during said dynamic computed tomography examination.

11. A computed tomography apparatus as claimed in claim 10 wherein said control unit is configured to coordinate the back and forth movement of said support plate between said first and second support plate end positions and the back and forth movement of said diaphragm elements between said first and second diaphragm element end positions to give said dose of x-ray radiation a substantially rectangular dose profile.

12. A computed tomography apparatus as claimed in claim 10, wherein said control unit, when moving said patient support plate back and forth between said first and second support plate end positions and collectively moving said diaphragm elements back and forth between said first and second diaphragm element end positions, is configured to always move said diaphragm elements and said patient support plate with respect to each other in opposite directions in the direction of said system axis.

13. A non-transitory, computer-readable data storage medium encoded with programming instructions for operating a computed tomography apparatus comprising a gantry having a stationary part and a rotatable part mounted at the stationary part to rotate around a system axis, an x-ray radiation source and an x-ray radiation detector mounted on the rotatable part opposite each other, said x-ray source emitting an x-ray beam that propagates in a direction toward said system axis, a diaphragm associated with said x-ray source and comprising diaphragm elements that are movable with respect to each other to limit a size of said x-ray beam and that are collectively movable in a direction of said system axis, and a patient support plate movable in a direction of said system axis, said storage medium being loaded into a control unit of said computed tomography apparatus and said programming instructions causing said control unit to:
implement a dynamic computed tomography examination of a body region of a patient on said patient support plate by moving said patient support plate back and forth in said direction of said system axis between a first support plate end position and a second support plate end position;
while moving said patient support plate back and forth between said first and second support plate end positions, collectively move said diaphragm elements of said diaphragm also in said direction of said system axis back and forth between a first diaphragm element end position and a second diaphragm element end position; and
coordinate the back and forth movement of said support plate between said first and second support plate end positions and the back and forth movement of said diaphragm elements between said first and second diaphragm element end positions to homogenize a dose of x-ray radiation applied to the patient by said x-ray beam during said dynamic computed tomography examination.

14. A non-transitory, computer-readable data storage medium as claimed in claim 13, wherein said programming instructions cause said control unit to:
when moving said patient support plate back and forth between said first and second support plate end positions and collectively moving said diaphragm elements back and forth between said first and second diaphragm element end positions, always move said diaphragm elements and said patient support plate with respect to each other in opposite directions in the direction of said system axis.

15. A non-transitory, computer-readable data storage medium as claimed in claim 13 wherein said programming instructions cause said control unit to coordinate said back and forth movement of said support plate between said first and second support plate end positions and the back and forth movement of said diaphragm elements between said first and second diaphragm element end positions to give said dose of x-ray radiation a substantially rectangular dose profile.

* * * * *